United States Patent [19]

Cuilty-Siller

[11] Patent Number: 5,994,407

[45] Date of Patent: Nov. 30, 1999

[54] PROCEDURE TO PREPARE A SOLUTION WITH CAPSAICIN

[76] Inventor: Carlos Cuilty-Siller, Rio San Juan #103 2° Piso Col. Miravalle, 64640 Monterrey, N.L., Mexico

[21] Appl. No.: 09/333,657

[22] Filed: Jun. 16, 1999

[51] Int. Cl.$^6$ .................................................. A61K 31/16
[52] U.S. Cl. ............................................................ 514/627
[58] Field of Search .............................................. 514/627

[56] References Cited

U.S. PATENT DOCUMENTS

| | | | |
|---|---|---|---|
| 4,997,853 | 3/1991 | Bernstein | 514/626 |
| 5,178,879 | 1/1993 | Adekunle et al. | 424/484 |
| 5,869,533 | 2/1999 | Holt | 514/627 |

*Primary Examiner*—Raymond Henley, III
*Attorney, Agent, or Firm*—Lawrence R. Brown

[57] ABSTRACT

The present invention refers to a procedure to prepare a Capsaicin solution in various steps, preferentially three; the first steps consists in the preparation of the solution "A" by mixing 80 milliliters of saline solution, 10 milliliters of polyoxyenthylenesorbitan monooleate and 10 milliliters of paraffin oil. Later on, the second stage is the preparation of solution "B" by mixing 3 milligrams of 8-Methyl-N-Vanillyl-6-Nonenamide in 100 milliliters of the solution "A". Finally the third stage includes the preparation of solution "C" mixing 10 milliliters of solution "B" in 90 milliliters of solution "A" in order to obtain a 10-micromolar concentration of 8-Methyl-N-Vanillyl-6-Nonenamide.

1 Claim, No Drawings

PROCEDURE TO PREPARE A SOLUTION WITH CAPSAICIN

BACKGROUND OF THE INVENTION

The Capsaicin (8-Methyl-N-Vanillyl-6-Nonenamide) is the active pungent of the Solenaceae family plants; it interacts with the umnyelinated C Fibers of the Trigeminal Nerve. The repeated topical application produces a selective and temporary destruction of the unmyelinated C Fibers, desensitizing the nasal cavity against some external stimuli, keeping intact the nasal reflexes.

This effect has been demonstrated by stimulating the nasal cavity in laboratory animals, measuring the levels of Substance P from the nasal secretions, and at the Nucleus of the Trigeminal Nerve in the brain stem.

The Subsance P is a peptide which acts as a neurotransmitter, it is located in large amounts in the nasal cavity, and it is released by the unmyelinated C Fibers of the Trigeminal Nerve in response to a wide variety of stimuli including thermal, mechanical and chemical stimuli.

DESCRIPTION OF THE INVENTION

It is described a procedure to prepare a topical intranasal 10 micromolar solution of capsaicin.

First three solutions are prepared named: A, B and C.

The solution "A" is prepared by mixing 80 milliliters of saline solution, 10 milliliters of polyoxyenthylenesorbitan monooleate, and 10 milliliters of parafin oil.

The solution "B" is prepared by mixing 3 milligrams of 8-Methyl-N-Vanillyl-6-Nonenamide in 100 milliliters of solution "A".

The solution "C" is prepared by mixing 10 milliliters of solution "B" in 90 milliliters of solution "A" to obtain a solution with a 10-micromolar concentration of 8-Methyl-N-Vanillyl-6-Nonenamide.

The combination of the fore solutions finally results in a solution with the desired concentration of capsaicin, which is the objective of this invention.

The combination of the fore solutions It will be used to treat patients withchronic non-inflammatory rhinitis and also in patients with rhinogenic headache.

What is claimed is:

1. A procedure to prepare a solution with Capsaicin characterized by a first stage in which a solution "A" is prepared by mixing 80 milliliters of saline solution, 10 milliliters of polyoxyenthylenesorbitan monooleate and 10 milliliters of paraffin oil, a second stage in which a solution "B" is prepared, by dissolving 3 milligrams of 8-Methyl-N-Vanillyl-6-Nonenamide in 100 milliliters of solution "A", and a third stage in which a solution "C" is prepared by mixing 10 milliliters of solution "B" in 90 milliliters of solution "A" to obtain a 10 micromolar concentration of 8-Methyl-N-Vanillyl-6-Nonenamide.

* * * * *